United States Patent [19]
Stevens

[11] Patent Number: 5,678,551
[45] Date of Patent: Oct. 21, 1997

[54] STERILIZABLE ULTRASOUND PROBE

[75] Inventor: Richard Barry Stevens, Chelmsford, Mass.

[73] Assignee: Hewlett-Packard Company, Palo Alto, Calif.

[21] Appl. No.: 651,028

[22] Filed: May 21, 1996

[51] Int. Cl.$^6$ ............................................. A61B 8/00
[52] U.S. Cl. .......................... 128/660.01; 128/662.03
[58] Field of Search ....................... 128/660.01, 662.03, 128/660.06, 897–898; 607/37; 439/191

[56] References Cited

U.S. PATENT DOCUMENTS

| | | | |
|---|---|---|---|
| 5,181,514 | 1/1993 | Solomon et al. | 128/660.09 |
| 5,279,308 | 1/1994 | DiSabito et al. | 128/748 X |
| 5,476,107 | 12/1995 | Oakley et al. | 128/898 X |

Primary Examiner—Francis Jaworski

[57] ABSTRACT

An ultrasound probe includes an electrical cable having a first end and a second end, an ultrasound transducer connected to the first end of the cable and a connector assembly connected to the second end of the cable. The connector assembly includes a connector housing having a cable opening and a mating connector opening, a connector body assembly mounted within the connector housing, a removable cover assembly sealed to the connector housing and covering the mating connector opening, and a strain relief assembly for sealing the cable opening between the cable and the connector housing. When the removable cover assembly is sealed to the connector housing, the connector assembly is immersible in a liquid, such as a sterilization fluid. The cover assembly is removed from the connector housing for operation of the ultrasound probe with an imaging system.

17 Claims, 6 Drawing Sheets

STERILIZABLE ULTRASOUND PROBE

FIELD OF THE INVENTION

This invention relates to ultrasound probes and, more particularly, to a connector assembly for an ultrasound probe. The connector assembly has a sealed configuration so that the ultrasound probe can be immersed in a sterilization fluid.

BACKGROUND OF THE INVENTION

Transesophegeal echo cardiography is an established technique in the area of cardiac imaging and involves the insertion of an ultrasound probe into a patient's esophagus to scan the heart from inside the esophagus. The transesophegeal ultrasound probe includes a multiple conductor electrical cable, an ultrasound transducer array connected to the distal end of the cable and a connector assembly attached to the proximal end of the cable. The probe may include a control mechanism for mechanically manipulating the ultrasound transducer to obtain images of the heart along different scan planes. The connector assembly is attached to an ultrasound imaging system. The distal end of the probe is inserted into the patient's esophagus to a desired location, and an ultrasound image is obtained. Transesophegeal ultrasound probes are disclosed, for example, in U.S. Pat. No. 5,181,514 issued Jan. 26, 1993 to Solomon et al.

The transesophegeal ultrasound probe is reusable and must be thoroughly cleaned after each use to prevent contamination between patients. One approach has been to treat such probes with an antiseptic such as glutaraldehyde. However, this antiseptic may have undesirable side effects and does not sterilize the probe. Another approach has been to sterilize the probe in ethylene oxide. However, ethylene oxide causes deterioration of the probe and cannot be used more than a few times, A sterilization unit sold by Steris Corporation involves placing an item to be sterilized in a closed container with a sterilant. The Steris procedure requires that the item being sterilized be sealed water-tight. Prior art electrical connectors utilized on transesophegeal ultrasound probes have been designed without consideration of sealing. The pins of the connector are exposed for engaging a mating connector on the imaging system.

SUMMARY OF THE INVENTION

According to the present invention, an ultrasound probe is provided. The ultrasound probe comprises an electrical cable having a first end and a second end, an ultrasound transducer operatively connected to the first end of the cable and a connector assembly operatively connected to the second end of the cable. The connector assembly comprises a connector housing having a cable opening and a mating connector opening, a connector body assembly mounted within the connector housing, a removable cover assembly including a cover sealed to the connector housing and covering the mating connector opening, and a strain relief assembly for sealing the cable opening between the cable and the connector housing. The ultrasound probe, including the connector assembly, is immersible in a liquid, such as a sterilization fluid.

The removable cover assembly preferably includes an elastomer gasket for sealing the cover to the connector housing. The cover assembly preferably further includes a latch mechanism for securing the removable cover assembly to the connector housing. The latch mechanism may include a helical, rotatable cam which engages a lip on the connector body assembly and compresses the elastomer gasket when rotated from an unlatched position to a latched position.

The cover assembly may further include a quick release fitting which permits the interior of the connector assembly to be pressurized. The connector assembly may be leak tested prior to sterilization.

The strain relief assembly may comprise an adapter sealed in the cable opening by at least one elastomer ring, a resilient inner sleeve coaxially positioned within the adapter and sealed to the adapter by at least one elastomer ring, a flexible strain relief sealed to the cable and to the inner sleeve, and a strain relief nut for retaining the adapter and the inner sleeve within the cable opening of the connector housing.

According to another aspect of the invention, a connector assembly for attachment to an electrical cable of a medical probe is provided. The connector assembly comprises a connector housing having a cable opening and a mating connector opening, a connector body assembly mounted within the connector housing, a removable cover assembly sealed to the housing and covering the mating connector opening, and a strain relief assembly for sealing the cable opening between the cable and the connector housing. The connector assembly is immersible in a liquid, such as a sterilization fluid, when it is installed on an electrical cable.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
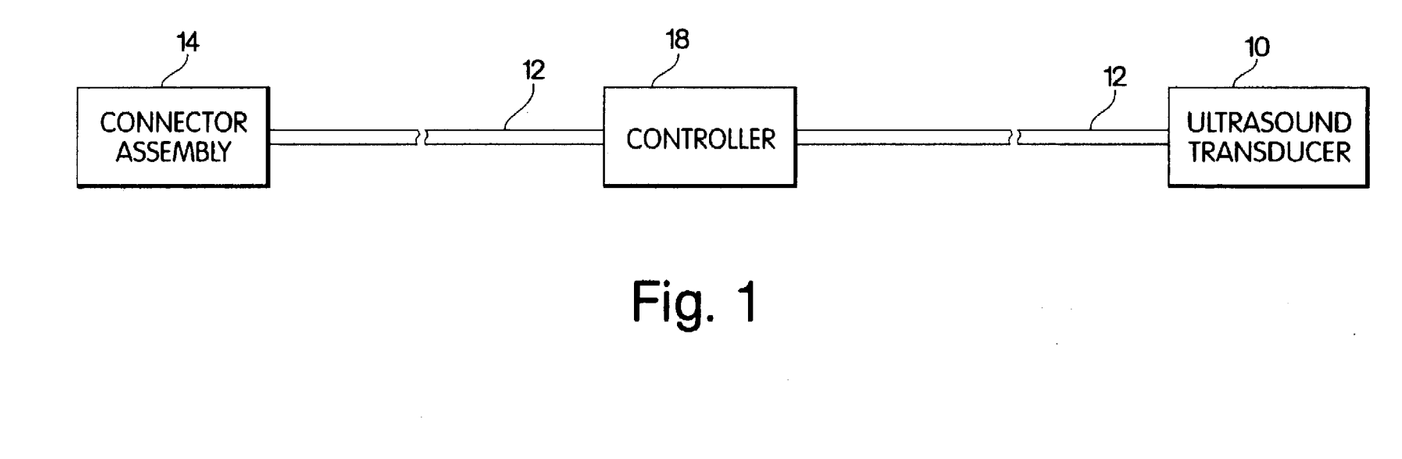
FIG. 1 is a schematic diagram of a transesophegeal ultrasound probe.

A schematic diagram of a transesophegeal ultrasound probe is shown in FIG. 1. An ultrasound transducer 10 is mounted at the distal end of a cable 12, which may, for example, extend through a gastroscope. The ultrasound transducer 10 may, for example, be an array of transducer elements used for phased array imaging. The cable 12 includes a plurality of electrical conductors, preferably miniature coaxial cables, for interconnecting the transducer elements to an ultrasound imaging system. A connector assembly 14 is connected to the proximal end of cable 12. The connector assembly 14 includes multiple connector pins and is used for interconnecting the probe to an ultrasound imaging system. The ultrasound probe may include a control handle 18 which is used for mechanically manipulating the ultrasound transducer 10 within the esophagus to obtain images along different scan planes. The distal end of the ultrasound probe is configured to be inserted into the esophagus of a patient. In a preferred embodiment, the portion of the ultrasound probe between control handle 18 and ultrasound transducer 10 comprises a gastroscope, and the conductors of cable 12 extend through the gastroscope to the transducer elements of ultrasound transducer 10. However, the present invention is not limited to a gastroscope or to an ultrasound probe, and may be used with any medical probe that requires a sealed connector assembly. An example of an ultrasound probe of the type shown, not including a sealed connector assembly, is the model 21364 Omni-I manufactured and sold by Hewlett-Packard Company.

As indicated above, the ultrasound probe is reusable and should be disinfected or sterilized after each use. The ultrasound transducer 10, the cable 12 and the control handle 18 are permanently sealed to prevent entry of foreign matter, as well as entry of the sterilant. The connector assembly 14 is not sealed during imaging, but must be sealed during sterilization so that the entire ultrasound probe is immersible in a liquid and may be placed in a sterilization container. The ultrasound probe may be sterilized in a System 1 sterilization system sold by Steris Corporation.

A sealed connector assembly in accordance with the invention is shown in FIGS. 2–7. The major components of the connector assembly 14 include a connector housing 20, a connector body assembly 22 mounted within the connector housing 20, a cover assembly 32 and a strain relief assembly 44. The cover assembly 32 is used to seal the connector assembly 14 during sterilization and is removed from housing 20 during ultrasound imaging so that the probe may be connected to an ultrasound imaging system. The connector body 20 includes a cable opening 34 through which cable 12 enters the connector assembly and a mating connector opening 36 for engagement of connector assembly 14 with a mating connector of the imaging system (with the cover assembly 32 removed).

Figure 2:
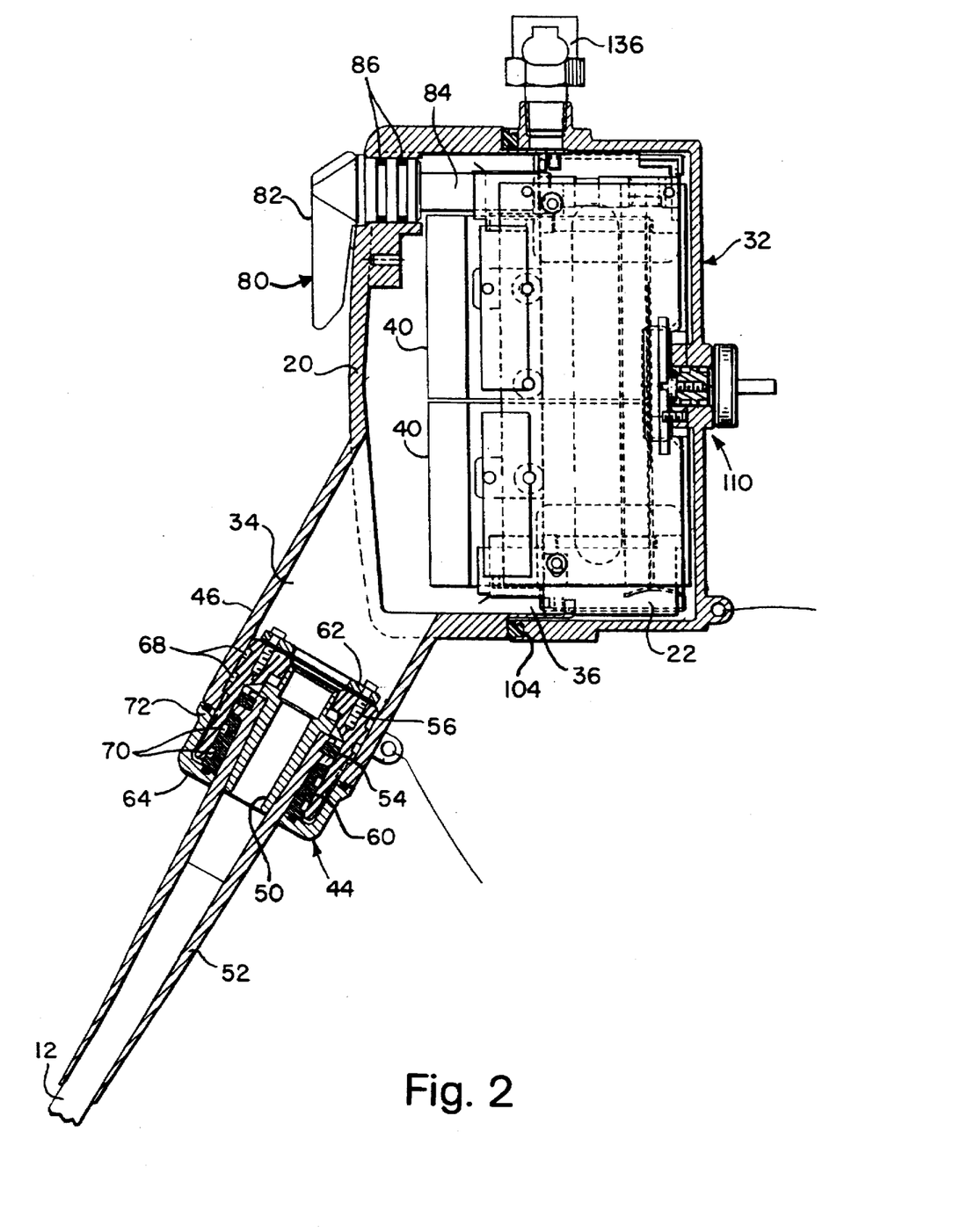
FIG. 2 is a cross-sectional view of a sealed connector assembly in accordance with the present invention.

The connector body assembly 22 includes a plurality of connector pins (not shown) mounted in a connector block. The connector pins are exposed for engaging a mating connector in the ultrasound imaging system when the connector assembly 14 is not sealed for sterilization. The connector body assembly 22 preferably further includes shield members 28 and 30 which surround the connector block 26 and provide RF shielding and grounding of the assembly. The connector body assembly 22 may further include miniature printed circuit boards 40 for mounting of circuit elements and for interconnection of the conductors in cable 12 to the connector pins.

In a preferred embodiment, the connector pins have a zero insertion force configuration. The connector assembly 14 further includes an actuator 80 for actuating the connector pins to and between connect positions in which the connector pins are engaged with corresponding conductors of a mating connector and disconnect positions in which the connector assembly may easily be removed from or attached to a mating connector. Zero insertion force connectors are known in the art and are commercially available. The actuator 80 includes an actuator handle 82 and an actuator pin 84 which extends through connector housing 20 to the connector body assembly 22. The actuator pin 84 is preferably sealed to connector housing 20 by elastomer rings 86. The zero insertion force connector pins may be of conventional design.

The strain relief assembly 44 relieves strain in cable 12 at the entrance of cable 12 into the connector assembly and seals the entrance of cable 12 into the connector assembly 14. The connector housing 20 includes a generally cylindrical cable entry portion 46 which defines cable opening 34. The strain relief assembly 44 is mounted in cable opening 34. The strain relief assembly 44 includes a tapered sleeve 50, which may be aluminum, coaxially positioned within a tapered strain relief 52. The strain relief 52 may be molded of a flexible material such as polyvinyl chloride (PVC). A washer 54, preferably fabricated of aluminum, is positioned in a groove in strain relief 52. The sleeve 50 and the strain relief 52 are coaxially mounted within an adapter 56, which may be fabricated of aluminum, The adapter 56 is secured within the cable entry portion 46 of connector housing 20. Preferably, the adapter 56 and the inside surface of cable entry portion 46 have mating flat portions which prevent rotation of the strain relief assembly 44 with respect to connector housing 20. A sleeve 60, preferably fabricated of PVC, is located between the outer surface of strain relief 52 and inner surface of adapter 56 to provide a seal between strain relief 52 and adapter 56. The inside surface of sleeve 60 is tapered in diameter to match the exterior surface of strain relief 52. An annular clamp plate 62 is mounted to the upper surface of adapter 56 within connector housing 20. The clamp plate 62 is used for electrically connecting the ground conductors of the coaxial cables within cable 12 to the adapter 56. The adapter 56 is in electrical contact with the connector housing 20. A cup-shaped strain relief nut 64 is threaded onto the outer surface of adapter 56 and the abuts against the end of cable entry portion 46. The strain relief nut 64 retains the strain relief assembly 44 within connector housing 20.

The elements of the strain relief assembly 44 are preferably sealed by elastomer rings to prevent entry of fluids into the interior of connector housing 20. In particular, adapter 56 is sealed to the inside surface of cable entry portion 46 by elastomer rings 68. Sleeve 60 is sealed to the inside surface of adapter 56 by elastomer rings 70. Strain relief nut 64 is sealed to cable entry portion 46 by elastomer ring 72 and is sealed to sleeve 60 by elastomer ring 74. Preferably, the sleeve 60 is solvent bonded to strain relief 52, and strain relief 52 is solvent bonded to cable 12 so as to provide sealing between these elements. The configuration of the strain relief assembly 44 provides reliable sealing against entry of fluids into the interior of connector housing 20 between cable 12 and housing 20.

To remove the strain relief assembly 44 from the connector housing 20, the connector body assembly 22 is removed from the connector housing 20, and strain relief nut 64 is removed from adapter 56. Then, the connector housing 20 slides along cable 12, and both the connector body assembly 22 and the strain relief assembly 44 are exposed. This allows access to calibration pots on printed circuit boards 40.

Figure 5:
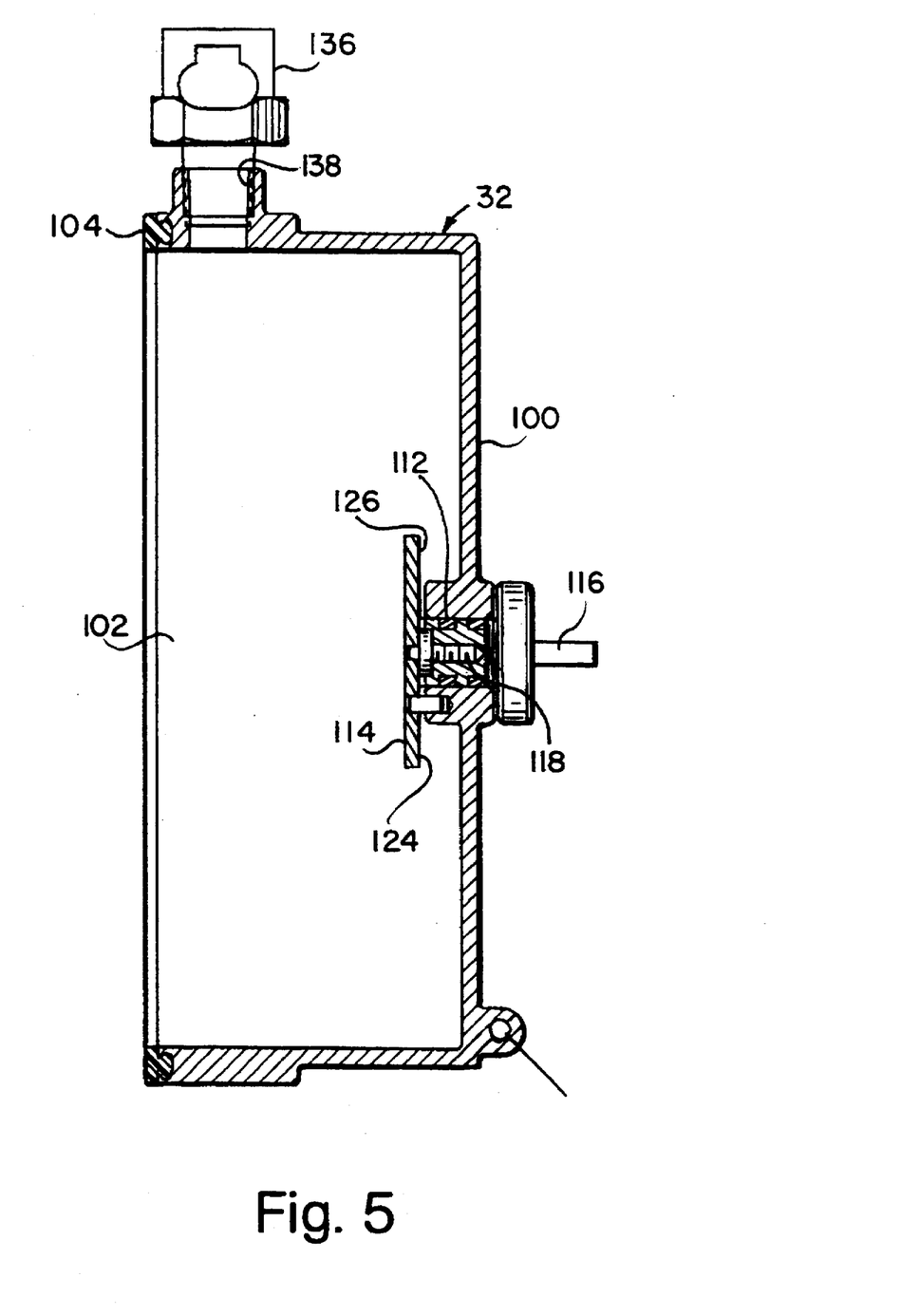
FIG. 5 is a cross-sectional view of the removable cover assembly shown in FIG. 2.
Figure 6:
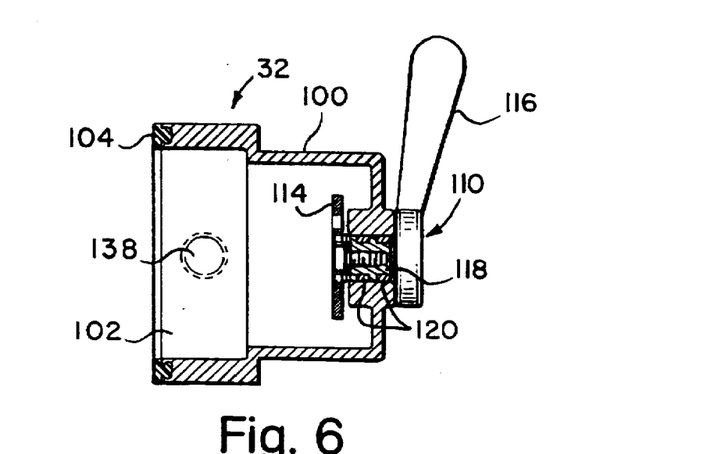
FIG. 6 is a cross-sectional view of the removable cover assembly taken along the line 6—6 of FIG. 5.
Figure 7:
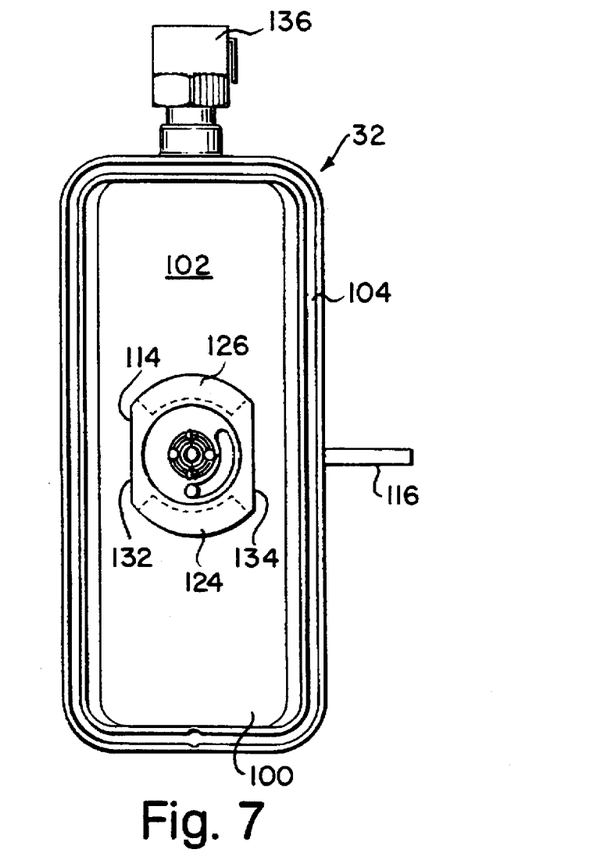
FIG. 7 shows the cover assembly as viewed from the open side thereof.

As indicated above, the cover assembly 32 is attached to the connector housing 20 so as to seal the connector assembly 14 for sterilization. The cover assembly 32 may be left in place when the ultrasound transducer 10 is not in use to protect connector pins 24. The cover assembly 32 includes a generally rectangular cover 100 having an open side 102. The periphery of open side 102 is provided with a groove for mounting a gasket 104. The gasket 104 may, for example, be fabricated of silicone rubber of 40 durometer Shore A and have 3 ridges for redundant sealing. The gasket 104 provides a seal between lip 106 (FIG. 4) on connector housing 20 and cover 100.

Figure 3A:
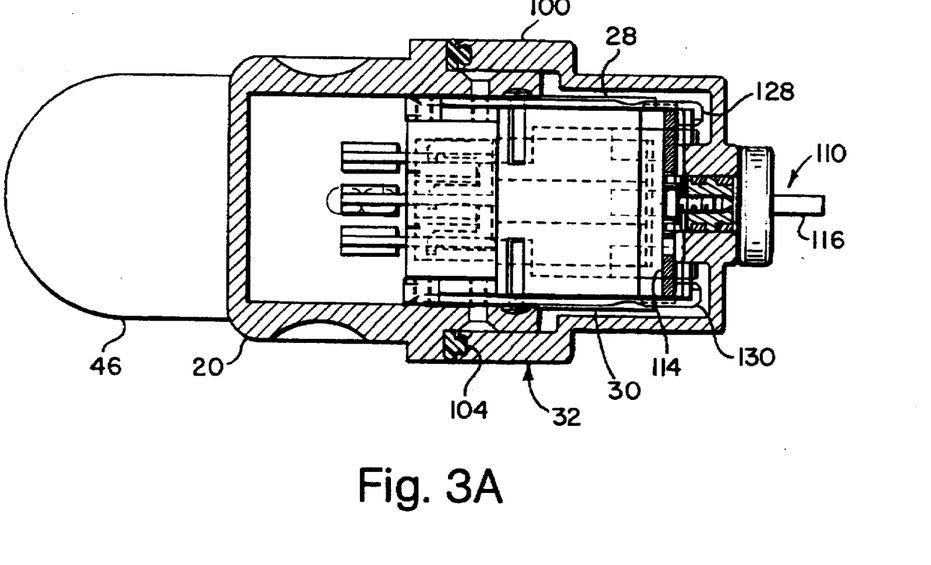
FIGS. 3A and 3B are cross-sectional views of the sealed connector assembly of FIG. 2 with the cover locked and with the cover unlocked, respectively.
Figure 3B:
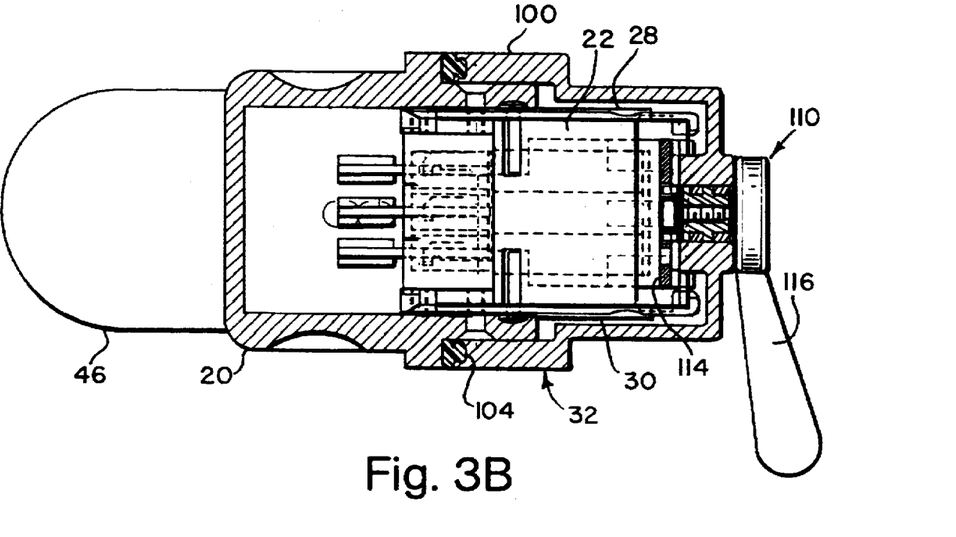
Figure 4:
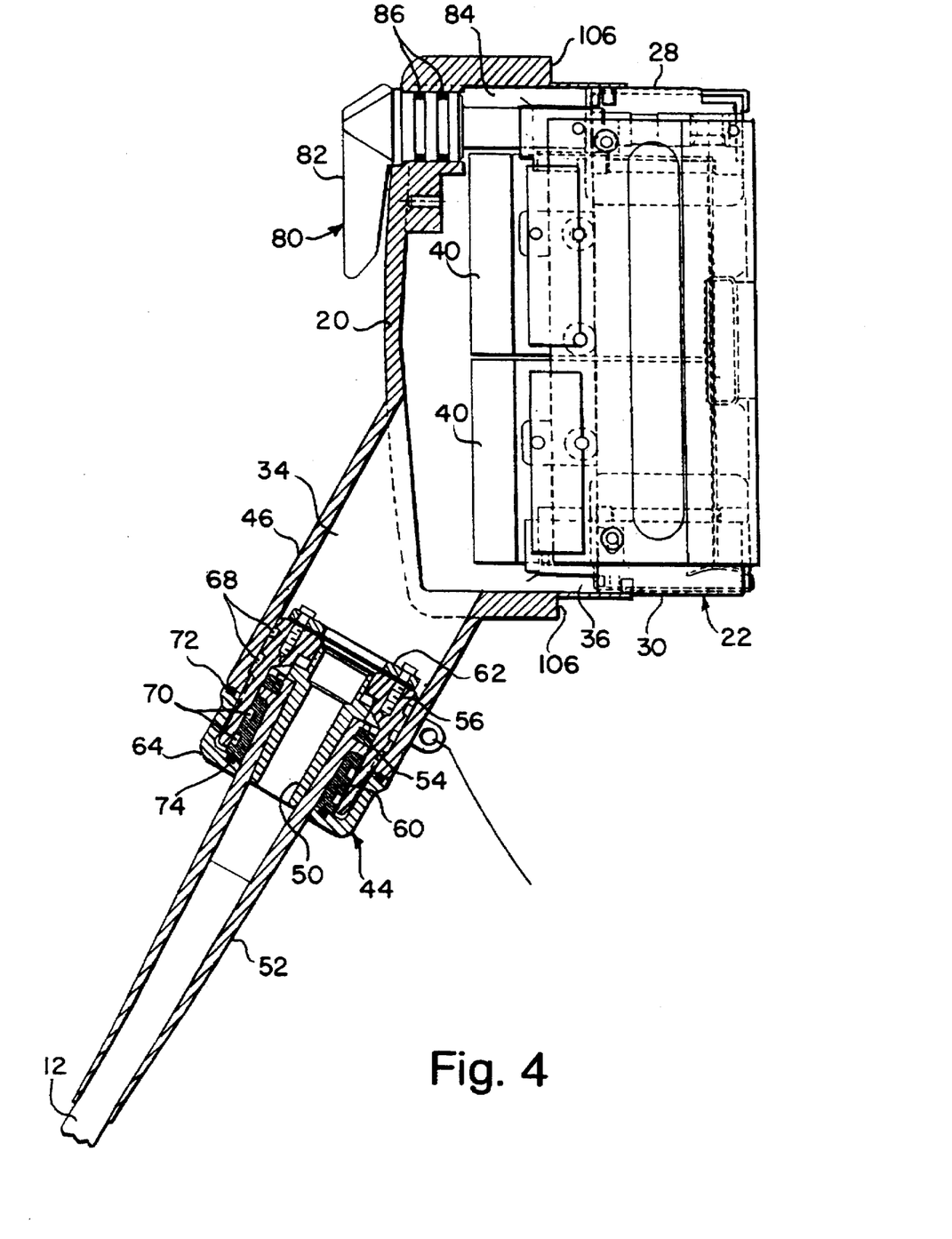
FIG. 4 is a cross-sectional view of the connector assembly of FIG. 2 with the cover removed.

A latch mechanism 110 is used to secure cover assembly 32 to connector housing 20. The latch mechanism 110 is mounted in an opening 112 in cover 100 located opposite open side 102. The latch mechanism includes a cam 114 positioned within cover 100, a latch handle 116 located externally of cover 100 and a latch pin 118 interconnecting cam 114 and latch handle 116 through opening 112. The latch pin 118 is preferably sealed to cover 100 by elastomer rings 120. The cam 114 is provided with helical cam surfaces 124 and 126 (FIG. 5) which engage corresponding lips 128 and 130, respectively, on the shield members 28 and 30 of the connector body assembly 22, as best shown in FIGS. 3A and 3B. The helical cam surfaces 124 and 126 may, for example, have a rise of 0.030 inch over a 120° turn. The cam 114 further includes flat portions 132 and 134 between cam surfaces 124 and 126. The flat portions 132 and 134 provide clearance with respect to lips 128 and 130 when the latch mechanism 110 is unlocked for installation or removal of the cover assembly 32. The cam provides approximately 0.030 inch compression of the gasket 104 for 120° rotation of the cam 114, when the cover assembly 32 is locked on the connector housing 20.

In the disclosed embodiment, the latch mechanism 110 may be rotated by 120° between the locked position shown in FIG. 3A and the unlocked position shown in FIG. 3B. In the unlocked position, the latch handle 116 extends from the side of the connector assembly and prevents the cover from being placed on the sterilization container. This configuration insures that the connector assembly is locked and sealed for sterilization.

It will be understood that different latch mechanisms may be used within the scope of the present invention. Furthermore, the latch mechanism may engage any convenient element of the connector housing 20 or the connector body assembly 22 to provide a secure attachment of the cover assembly to the connector housing.

Cover assembly 32 preferably further includes a quick release fitting 136 which may be mounted in a threaded opening 138 in cover 100. The quick release fitting 136 may, for example, be a type PMCD10-0-12 available from Colder Products Company, which is normally closed except when an external device is attached to it. The quick release fitting 136 may be connected to a pressurizing device (not shown) for pressurizing the interior of the connector assembly 14 to a pressure of about 1-2 PSI. The connector assembly 14 may then be leak tested by immersing it in water to verify the integrity of the seal prior to sterilization. The interior of connector assembly 14 is interconnected to the interior region of cable 12, control handle 18 and ultrasound transducer 10. Thus, the entire ultrasound transducer assembly can be leak tested by applying a desired pressure through quick release fitting 136.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An ultrasound probe comprising:

an electrical cable having a first end and a second end;

an ultrasound transducer operatively connected to the first end of said cable; and a connector assembly operatively connected to the second end of said cable, said connector assembly comprising:

a connector housing having a cable opening and a mating connector opening;

a connector body assembly mounted within said connector housing and coupled to said cable;

a removable cover assembly including a cover sealed to said connector housing and covering said mating connector opening, said cover assembly being portable so that it is readily movable with said connector housing and may remain attached to said connector housing before, during and after immersion in a liquid; and a strain relief assembly for sealing said cable opening between said cable and said connector housing, wherein said connector assembly is immersible in the liquid.

2. An ultrasound probe as defined in claim 1 wherein said removable cover assembly includes an elastomer gasket for sealing said cover to said connector housing.

3. An ultrasound probe as defined in claim 2 wherein said cover assembly further includes a latch mechanism for securing said removable cover assembly to said connector housing.

4. An ultrasound probe as defined in claim 3 wherein said latch mechanism includes a device for compressing said elastomer gasket when said cover is sealed to said connector housing.

5. An ultrasound probe as defined in claim 3 wherein said latch mechanism includes a helical, rotatable cam which engages a lip on said connector body assembly and compresses said elastomer gasket when rotated from an unlatched position to a latched position.

6. An ultrasound probe as defined in claim 5 wherein said latch mechanism further includes a latch handle external to said connector housing, a latch pin interconnecting said latch handle and said latch cam, and at least one elastomer ring for sealing said latch pin to said cover.

7. An ultrasound probe as defined in claim 1 wherein said cover assembly further includes a quick release fitting that permits an interior region of said connector assembly to be pressurized.

8. An ultrasound probe as defined in claim 1 wherein said connector assembly further includes an actuator for actuating connector pins in said connector body assembly, said actuator including an actuator handle external to said connector housing, an actuator pin extending through said connector housing to said connector body assembly and at least one elastomer ring for sealing said actuator pin to said connector housing.

9. An ultrasound probe as defined in claim 1 wherein said strain relief assembly comprises an adapter sealed in said cable opening by at least one elastomer ring, a resilient inner sleeve coaxially positioned within said adapter and sealed to said adapter by at least one elastomer ring, a flexible strain relief sealed to said cable and to said inner sleeve, and a strain relief nut for retaining said adapter and said inner sleeve within said cable opening.

10. A connector assembly for attachment to an electrical cable of a medical probe comprising:

a connector housing having a cable opening and a mating connector opening;

a connector body assembly mounted within said connector housing;

a removable cover assembly including a cover sealed to said housing and covering said mating connector opening, said cover assembly being portable so that it is readily movable with said connector housing and may remain attached to said connector housing before, during and after immersion in a liquid; and a strain relief assembly for sealing said cable opening between said cable and said connector housing, wherein said connector assembly is immersible in the liquid when installed on an electrical cable.

11. A connector assembly as defined in claim 10 wherein said removable cover assembly includes an elastomer gasket for sealing said cover to said connector housing.

12. A connector assembly as defined in claim 11 wherein said cover assembly further includes a latch mechanism for securing said removable cover assembly to said connector housing.

13. A connector assembly as defined in claim 12 wherein said latch mechanism includes a helical, rotatable cam which engages a lip on said connector body assembly and compresses said elastomer gasket when rotated from an unlatched position to a latched position.

14. A connector assembly as defined in claim 13 wherein said latch mechanism further includes a latch handle external to said connector housing, a latch pin interconnecting said latch handle and said cam, and at least one elastomer ring for sealing said latch pin to said cover.

15. A connector assembly as defined in claim 10 wherein said cover assembly further includes a quick release fitting that permits an interior region of said connector assembly to be pressurized.

16. A connector assembly as defined in claim 10 wherein said connector assembly further includes an actuator for actuating connector pins in said connector body assembly, said actuator including an actuator handle external to said connector housing, an actuator pin extending through said connector housing to said connector body assembly and at least one elastomer ring for sealing said actuator pin to said connector housing.

17. A connector assembly as defined in claim 10 wherein said strain relief assembly comprises an adapter sealed in said cable opening by at least one elastomer ring, a resilient inner sleeve coaxially positioned within said adapter and sealed to said adapter by at least one elastomer ring, a flexible strain relief sealed to said inner sleeve and a strain relief nut for retaining said adapter and said inner sleeve within said cable opening.

* * * * *